United States Patent [19]

Mallion et al.

[11] 4,079,055

[45] Mar. 14, 1978

[54] CHEMICAL REDUCTION PROCESS

[75] Inventors: Keith Blakeney Mallion; Graham Ernest Robinson, both of Macclesfield, England

[73] Assignee: Imperial Chemical Industries Limited, London, England

[21] Appl. No.: 688,548

[22] Filed: May 21, 1976

[30] Foreign Application Priority Data

Jun. 11, 1975 United Kingdom ............... 25012/75

[51] Int. Cl.$^2$ ............................................ C07C 177/00
[52] U.S. Cl. .................................... 542/426; 560/121; 560/55; 560/53; 260/343.41; 260/343.3 P; 260/448.2 R; 260/514 D; 260/520 R
[58] Field of Search .......... 260/468 D, 514 D, 342 F, 260/343.3 P, 240 R, 448.2 R, 520 R, 473 R

[56] References Cited

U.S. PATENT DOCUMENTS 3,846,475  11/1974  Crabbe et al. .................. 260/468 D

OTHER PUBLICATIONS

Corey et al., J.A.C.S., 94, pp. 8616–8618, 1972.

Primary Examiner—Lorraine A. Weinberger
Assistant Examiner—Jane T. Fan
Attorney, Agent, or Firm—Cushman, Darby & Cushman

[57] ABSTRACT

The disclosure relates to a novel chemical process whereby enone intermediates for prostaglandins are reduced steroselectively to the α-enols, the α-hydroxy of which corresponds to the prostaglandin 15α-hydroxy group.

7 Claims, No Drawings

CHEMICAL REDUCTION PROCESS

This invention relates to a chemical reduction process, and in particular it relates to a novel chemical process for the stereoselective reduction of prostaglandin intermediates, containing a 15-oxo group, predominantly to the preferred 15-hydroxy epimer.

In a widely used synthesis of prostaglandins and prostaglandin-like compounds, one stage involves the reduction of a ketone I to a mixture of epimeric α- and β-alcohols II ($R^1$ = C-16 and onwards of a known prostaglandin or prostaglandin-like compound, $R^2$ is a carboxylic acyl group, for example 4-phenylbenzoyl):

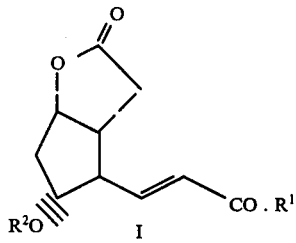

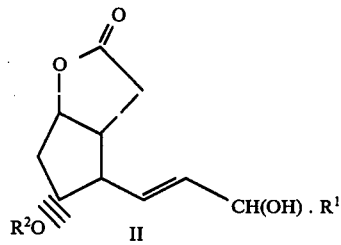

In the reduction processes normally used, the ketone is reduced non-stereoselectively to give a mixture of equal amounts of the α-hydroxy and β-hydroxy epimers, whereas, in the case of natural prostaglandins $E_1$, $E_2$, $F_1\alpha$ and $R_2\alpha$, and of synthetic analogues which are being developed now, it is only the 15α-hydroxy epimer which is considered to be useful. The normally used reduction processes are therefore unattractive for the commercial manufacture of these compounds because, together with the required α-hydroxy epimer, they produce an equal quantity of the unwanted β-hydroxy epimer.

There have been a few attempts to provide stereoselective reductions, for example those described in The Journal of The American Chemical Society, 1972, volume 94, pages 8616 to 8618, and in United Kingdom Patent Specification No. 1,384,865, but both suffer the disadvantage, from the point of view of commercial manufacture, of using an expensive, "bulky borohydride" type of reducing agent, while the former suffers additional disadvantages in requiring particularly bulky protecting groups in the substrate, and a reaction temperature of about −120° C. to −130° C. Such a temperature requires the use of liquefied gas cooling agents, which are hazardous and inconvenient for routine commercial manufacture. Furthermore, although the former process, with its bulky reagent, bulky protecting group and very low temperature, will give high stereoselectivity of up to about 90% of the required α-hydroxy epimer, the latter, more convenient process, which does not require the presence of a bulky protecting group or liquefied gas cooling, gives at best about 80% of the required α-hydroxy epimer.

It is therefore an object of the present invention to provide an improved reduction process which requires either no protecting group, or one which is easily and conveniently added and removed, which does not require liquefied gas cooling agents, and which gives a high stereospecificity of at least 75% of an α-hydroxy epimer.

Thus, according to the invention, there is provided a process for the manufacture of a mixture of epimers of the formula:

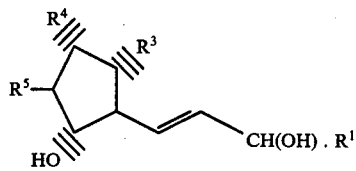

wherein $R^1$ is C-16 and onwards of a known prostaglandin or prostaglandin-like compound, either $R^3$ is a 6-carboxy-2-cis-hexenyl, 6-carboxyhexyl, 6-($C_{1-4}$alkoxycarbonyl)-2-cis-hexenyl, 6($C_{1-4}$alkoxycarbonyl)hexyl, 6-[tri($C_{1-4}$alkyl)silyloxycarbonyl]-2-cis-hexenyl or 6-[tri($C_{1-4}$alkyl)silyloxycarbonyl]hexyl radical and $R^4$ is a hydroxy radical, or $R^3$ and $R^4$, together with the two adjacent ring carbon atoms, form a lactone ring of the formula:

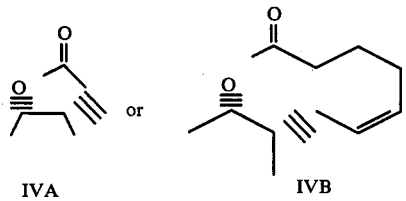

and $R^5$ is a hydrogen or iodine atom, which mixture comprises at least 80% of the side-chain α-hydroxy epimer, characterised in that a ketone of the formula:

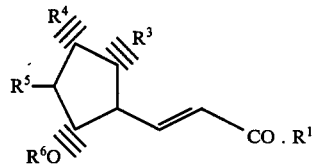

wherein $R^1$, $R^3$ and $R^5$ have the meanings stated above, $R^4$ has the meaning stated above, or is a tri-($C_{1-4}$alkyl)-silyloxy radical, and $R^6$ is a hydrogen atom, a tetrahydropyran-2-yl radical or a trialkylsilyl radical wherein each alkyl is of 1 to 4 carbon atoms, a tribenzylsilyl or a triphenylsilyl radical, is reduced with a di-isobornyloxy aluminum alkoxide, wherein the alkoxide part is of 1 to 4 carbon atoms, or di-isopropoxy aluminum diphenylmethoxide, in an inert solvent at a temperature between +25° C. and −80° C., whereafter, when $R^6$ is not a hydrogen atom, or when $R^4$ is a tri($C_{1-4}$alkyl)-silyoxy radical, the protecting group is hydrolysed under acidic conditions.

Particular values for $R^1$ are, for example, a $C_{4-7}$alkyl radical especially a n-pentyl radical, a phenoxymethyl radical, optionally substituted in the phenyl ring thereof with a halogen atom or a trifluoromethyl radical, and a pyridyloxy methyl radical optionally substituted by halogen. Particular phenoxymethyl radicals are a 3-chlorophenoxymethyl radical and a 3-trifluoromethylphenoxymethyl radical, and a particular pyridyloxy methyl radical is, for example, a 5-chloropyrid-2-yloxymethyl radical.

Particular trialkylsilyl radicals which may be used for $R^6$ are trimethylsilyl, triethylsilyl, tributylsilyl, triphenylsilyl, tribenzylsilyl, and t-butyldimethylsilyl radicals.

A preferred reducing agent is di-isobornyloxy aluminum isopropoxide.

Suitable inert solvents which may be used in the process of the invention are, for example, toluene, ethyl acetate and tetrahydrofuran, and mixtures of toluene and ethyl acetate, or toluene and tetrahydrofuran.

A convenient reaction temperature is about $-78°$ C. which is readily attained by using a cooling bath of solid carbon dioxide in acetone.

The practical utility of the process of the invention depends also upon the ease with which the minor proportion of the unwanted $\beta$-hydroxy epimer can be removed from the reaction product obtained.

In the manufacture of cloprostenol (III, $R^1$ = 3-chlorophenoxymethyl, $R^3$ = 6-carboxy-2-cis-hexenyl, $R^4$ = hydroxy, $R^5$ = hydrogen, side-chain $\alpha$-hydroxy epimer), up to 20% of the side-chain $\beta$-hydroxy epimer can be readily removed either by crystallization of the reaction product III ($R^1$ = 3-chlorophenoxymethyl, $R^3$, $R^4$ and the two adjacent ring carbon atoms form a ring of the formula IVA, $R^5$ = hydrogen, ring hydroxy protected as trialkysilyl ether), or by crystallisation of the final product (III, $R^1$ = 3-chlorophenoxymethyl, $R^3$ = 6-carboxy-2-cis-hexenyl, $R^4$ = hydroxy, $R^5$ = hydrogen).

In the manufacture of fluprostenol (III, $R^1$ = 3-trifluoromethylphenoxymethyl, $R^3$ = 6-carboxy-2-cis-hexenyl, $R^4$ = hydroxy, $R^5$ = hydrogen, side-chain $\alpha$-hydroxy epimer), up to 20% of the side-chain $\beta$-hydroxy epimer can be readily removed by crystallisation of the diol reaction product (III, $R^1$ = 3-trifluoromethylphenoxymethyl, $R^3$, $R^4$ and the two adjacent ring carbon atoms form a ring of the formula IVA, $R^5$ = hydrogen).

The invention is illustrated but not limited by the following Examples. High pressure liquid chromatography was carried out on a "Partisil" (trade mark) silica column, particle size 5μ, eluting with 25% acetonitrile in chloroform, to separate diol mixtures, hexane/absolute ethanol/acetic acid (93/6.5/0.5 parts by volume) to separate prostaglandin acid mixtures, or chloroform to separate silylated enol mixtures. The peaks of the chromatogram were detected by U.V. absorption at 275 nm.

EXAMPLE 1

4$\beta$-[4-(3-Chlorophenoxy)-3-oxo-1-trans-butenyl]-2,3,3a$\beta$,6a$\beta$-tetrahdyro-5$\alpha$-hydroxy-2-oxocyclopenteno[b]furan (168mg.) was dissolved in a mixture of tetrahydrofuran (1ml.) and toluene (1ml.), and the solution was stirred under argon at room temperature while toluene-p-sulphonic acid (6 crystals) was added, followed by 2,3-dihydropyran (126 μl.). After 2¼ hours, pyridine (few drops) was added.

The solution was allowed to stand at room temperature overnight, and was then cooled in an acetone/solid carbon dioxide bath to $-78°$ C. Di-isobornyloxy aluminum isopropoxide (2.5ml. of a 0.3M solution in toluene) was added over 5 minutes, and the mixture was stirred for 5 hours, water (1ml.) was added, and the solution was allowed to warm to room temperature overnight. Ethyl acetate (5ml.) and 2N hydrochloric acid (5ml.) were added, the organic layer was separated and dried, and the solvent was evaporated.

The residue was dissolved in methanol (5ml.) and toluene-p-sulphonic acid (6 crystals) was added. The mixture was stirred for 4½ hours, pyridine (2 drops) was added and the reaction mixture was evaporated to dryness. The residue consisted of 4$\beta$-[4-(3-chlorophenoxy)-3-hydroxy-1-trans-butenyl]-2,3,3a$\beta$,6a$\beta$-tetrahydro-5$\alpha$-hydroxy-2-oxocyclopenteno[b]furan which, on examination by high pressure liquid chromatography (HPLC), was shown to contain 83% of the 3$\alpha$-hydroxy epimer and 17% of the 3$\beta$-hydroxy epimer, by comparison with authentic samples.

A similar reduction carried out at room temperature gave 60% of 3$\alpha$-hydroxy epimer and 40% of 3$\beta$-hydroxy epimer.

Di-isobornyloxy aluminum isopropoxide is conveniently prepared from dl-isoborneol and aluminum tri-isopropoxide

EXAMPLE 2

The di-isobornyloxy aluminum isopropoxide reduction described in paragraphs 2 and 3 of Example 1 was repeated, using 4$\beta$-[4-(3-chlorophenoxy)-3-oxo-1-trans-butenyl]-2,3,3a$\beta$,6-a$\beta$-tetrahydro-2-oxo-5$\alpha$-(trimethylsilyloxy)cyclopenteno[b]furan as the starting material. The reduction was complete in 2¼ hours, and the protecting trimethylsilyl group was removed during the work-up by extracting the product into ethyl acetate (10ml.) and shaking the ethyl acetate extract with 2N hydrochloric acid (5ml.) for 2 minutes. The same product was obtained as in Example 1, and was shown by HPLC to consist of 93% of 3$\alpha$-hydroxy epimer and 7% of 3$\beta$-hydroxy epimer, by comparison with authentic samples.

The starting material used in the above process may be obtained as follows:

4$\beta$-[4-(3-Chlorophenoxy)-3-oxo-1-trans-butenyl]-2,3,3a$\beta$,6a$\beta$-tetrahydro-5$\alpha$-hydroxy-2-oxocyclopenteno[b]furan (3.36g.) was dissolved in tetrahydrofuran (20ml.) and toluene (20ml.) with stirring under argon. Hexamethyldisilazane (1.62g.) and trimethylchlorosilane (1.08g.) were added, and the mixture was stirred at room temperature under argon for 17 hours to give a solution of the trimethylsilyl ether starting material. This solution can be used in the reduction process without isolating the starting material.

A similar reduction carried out at $-15°$ C. gave 74% of 3$\alpha$-hydroxy epimer and 26% of 3$\beta$-hydroxy epimer.

EXAMPLE 3

The process described in Example 2 was repeated, except that the trimethylsilyl ether solution was evaporated to dryness. The residue was dissolved in ethyl acetate and the solution washed with brine to remove silicone by-products. The reduction was carried out in ethyl acetate solution at $-78°$ C. and was complete after 2½ hours. The trimethylsilyl protecting group was removed by shaking the ethyl acetate of the reaction product with hydrochloric acid, and the deprotected product was shown by HPLC to contain 87% of the 3$\alpha$-hydroxy epimer and 13% of the 3$\beta$-hydroxy epimer by comparison with authentic samples.

EXAMPLE 4

The reduction process described in Example 1 was repeated, using 5$\alpha$-(t-butyldimethylsilyloxy)-4$\beta$-[4-(3-chlorophenoxy)-3-oxo-1-trans-butenyl]-2,3,3a$\beta$,6a$\beta$-tetrahydro-2-oxocyclopenteno[b]furan as the starting material. The reaction was carried out in toluene, and was complete in 1 hour, and the protecting t-butyldimethylsilyl group was removed by evaporating the solvent from the product, dissolving the residue in methanol, adding toluene-p-sulphonic acid and stirring this reaction mixture at room temperature for 18 hours. Pyridine (2 drops) was added, and the whole was evaporated to dryness. The residue was dissolved in chloroform containing 25% of acetonitrile, and HPLC examination of this solution showed that the reaction product comprised 95% of 3α-hydroxy epimer and 5% of 3β-hydroxy epimer, by comparison with authentic samples.

The starting material used in the above process was obtained as follows:

4β-[4-(3-Chlorophenoxy)-3-oxo-1-trans-butenyl]-2,3,3aβ,6aβ-tetrahydro-5α-hydroxy-2-oxocyclopenteno[b]furan (337mg.) was dissolved in dimethylformamide (2ml.). t-Butyldimethylchlorosilane (362mg.) was added, and the mixture was stirred under argon at room temperature for 15 minutes, then imidazole (34mg.) was added. After 2 hours, ethyl acetate (5ml.) and water (5ml.) were added, and the mixture was allowed to stand overnight. Ethyl acetate (5ml.) was added, the ethyl acetate extract was separated, washed with saturated brine and dried, and the solvent was evaporated to give the required starting material.

A similar reduction to that described above was carried out at room temperature in a mixture of toluene and tetrahydrofuran. The reaction was complete in 1 hour, and the product comprised 76% of the 3α-hydroxy epimer and 24% of the 3β-hydroxy epimer.

EXAMPLE 5

The reduction process described in Example 1 was repeated using 4β-[4-(3-chlorophenoxy)-3-oxo-1-trans-butenyl]-2,3,3aβ,6aβ-tetrahydro-5α-hydroxy-2-oxocyclopenteno[b]furan as starting material. The reaction was carried out in a mixture of toluene and tetrahydrofuran and had gone to the extent of about 75% in 6 hours. The product was examined by thin-layer chromatography (t.l.c.) on silica gel eluted with methylene chloride containing 20% acetone, and shown to comprise 80% of 3α-hydroxy epimer and 20% of 3β-hydroxy epimer, by comparison with authentic samples.

EXAMPLE 6

The reduction process described in Example 1 was repeated, using 2,3,3aβ,6aβ-tetrahydro-5α-hydroxy-2-oxo-4β-[3-oxo-4-(3-trifluoromethylphenoxy)-1-trans-butenyl]-cyclopenteno[b]furan as the starting material. The reaction was carried out in a mixture of toluene and tetrahydrofuran and had gone to the extent of about 80% in 7 hours. The product was shown by t.l.c. on silica gel eluted with methylene chloride containing 20% acetone to comprise approximately 80% of the 3α-hydroxy epimer and approximately 20% of the 3β-hydroxy epimer, by comparison with authentic samples.

EXAMPLE 7

The reduction process described in Example 1 was repeated, using 2,3,3aβ,6aβ-tetrahydro-2-oxo-4β-[3-oxo-4-(3-trifluoromethylphenoxy)-1-trans-butenyl]-5α-(trimethylsilyloxy)cyclopenteno[b]furan as the starting material. The reaction was carried out in a mixture of toluene and tetrahydrofuran and was complete in 2 hours. The product, after removal of the protecting trimethylsilyl group, was shown by t.l.c. on silica gel eluted with methylene chloride containing 30% acetone to comprise approximately 90% of the 3α-hydroxy epimer and approximately 10% of the 3β-hydroxy epimer, by comparison with authentic samples.

EXAMPLE 8

The di-isobornyloxy aluminium isopropoxide reduction described in paragraph 2 of Example 1 was repeated, using silylated enone starting materials of the formula I ($R^2$ having the values shown in the table below), to give silylated enol products of the formula II. The proportion of α-hydroxy epimer to β-hydroxy epimer ($\alpha:\beta$) in the silylated enol product II, was determined by HPLC:

| $R^1$ | $R^2$ | Reaction time (hours) | $\alpha:\beta$ |
| --- | --- | --- | --- |
| 3-chlorophenoxymethyl | $(C_2H_5)_3Si$ | 2.25 | 96:4 |
| 3-chlorophenoxymethyl | $(n-C_4H_9)_3Si$ | 2.5 | 93:7 |
| 3-chlorophenoxymethyl | $(C_6H_5)_3Si$ | 5* | 90:10 |

*further portion of reducing agent added after 4 hours.

The triethylsilyl enone starting material of the formula I was prepared as follows:

4β-[4-(3-Chlorophenoxy)-3-oxo-1-trans-butenyl]-2,3,3aβ,6aβ-tetrahydro-5α-hydroxy-2-oxocyclopenteno[b]furan (169mg.) and dry toluene (1ml.) were stirred together under argon at room temperature, and dry dimethylformamide was added until a clear solution was obtained (300μl.). Pyridine (80μl.) was added, followed by triethylchlorosilane (168μl.), and the mixture was stirred at room temperature. After 17 hours more pyridine (40μl.) and triethylchlorosilane (84μl.) were added, and the stirring was continued for a further 6 hours. Water (5ml.) was then added, the mixture was extracted with ethyl acetate (10ml.), and the ethyl acetate was washed with a mixture (10ml.) of equal volumes of saturated brine and water. The extract was dried, the solvent was evaporated, and the residual colourless gum crystallised on standing, to give 4β-[4-(3-chlorophenoxy)-3-oxo-1-trans-butenyl]-2,3,3aβ,6aβ-tetrahydro-2-oxo-5α-triethylsilyloxycyclopenteno[b]furan, $R_F = 0.63$ (1:1 v/v toluene:ethyl acetate).

In the preparation of the tri-n-butylsilyl enone starting material, the process described above was repeated, using 1.69g. of the cyclopenteno[b]furan starting material, and using tri-n-butylchlorosilane (2.35g.) in place of triethylchlorosilane, the reaction was worked up after 17 hours, and the product was purified by column chromatography on kieselguhr (150g.), applying the material to the column in methylene dichloride solution and eluting with the same solvent. The first 850ml. of eluate was discarded, and the following 1800ml. was evaporated to give the tri-n-butylsilyl enone as a colourless oil, which solidified after drying for 2 hours at 0.1 mm. Hg., $R_F = 0.19$ (methylene dichloride); $R_F = 0.71$ (1:1 v/v toluene:ethyl acetate).

In the preparation of the triphenylsilyl enone starting material, the process described above was repeated, using 1.69g. of the cyclopenteno[b]furan starting material, and using triphenylchlorosilane (2.95g.) in place of triethylchlorosilane, the reaction was worked up after 24 hours, and the product was purified by column chromatography on kieselguhr (190g.), as described above for the tri-n-butyl compound. The first 1550ml. of eluate was discarded, and the following 1750ml. was evaporated to give the triphenylsilyl enone as a brittle white foam, which collapsed to a hard, pale yellow glass, $R_F$ = 0.13 (methylene dichloride), $R_F$ = 0.53 (1:1 v/v toluene:ethyl acetate).

EXAMPLE 9

The process described in Example 2 was repeated, using 16-(3-chlorophenoxy)-9α,11α-dihydroxy-15-oxo-17,18,19,20-tetranor-5-cis,13-trans-prostadienoic acid 1,9α-lactone as the starting material, and the reduction was stopped after 6 hours. The product was hydrolysed with aqueous methanolic potassium hydroxide to give 16-(3-chlorophenoxy)-9α,11α,15-trihydroxy-17,18,19,20-tetranor-5-cis,13-trans-prostadienoic acid containing 85% of the 15α-hydroxy epimer and 15% of the 15β-hydroxy epimer, by HPLC.

The lactone starting material may be prepared as follows:

7-[2β-Dimethoxymethyl-5α-hydroxy-3α-(tetrahydropyran-2-yloxy)cyclopent-1α-yl]hept-5-enoic acid (6.07g.) was dissolved in pyridine (40ml.) under argon, and treated with 4-phenylbenzoyl chloride (6.80g., 2equivalents), and the mixture was left at room temperature overnight. The pyridine was removed by azeotropic distillation with toluene, and the residue was partitioned between diethyl ether (200ml.) and saturated aqueous sodium bicarbonate solution (75ml.). The mixture was filtered to remove insoluble material, and the ether layer was separated and washed with more sodium bicarbonate solution (25ml.). The aqueous washings were combined and again extracted with diethyl ether (100ml.). The combined ether extracts were then washed with water (50ml.), saturated brine (50ml.) and dried, and the solvent was evaporated. The residue was again subjected to azeotropic distillation with toluene, then purified by column chromatography on magnesium silicate ("Florisil" — trade mark) eluting with toluene, and collecting 10ml. fractions. Fractions 5 to 36 were combined and the solvent was evaporated to give 7-[2β-dimethoxymethyl5α-hydroxy-3α-(tetrahydropyran-2-yloxy)cyclopent-1α-yl]hept-5-enoic acid lactone, $R_F$ = 0.58 (diethyl ether).

The lactone (1.98g.) was dissolved in dry methanol (30ml.), and toluene-p-sulphonic acid monohydrate (approximately 100mg.) was added. After 45 minutes, pyridine (0.7ml.) was added, the mixture was evaporated to dryness, and residual pyridine was removed by azeotropic distillation with toluene. The residue was partitioned between diethyl ether (50ml.) and saturated brine (10ml.), and the brine was separated and washed with more ether (50ml.). The ether extracts were combined and evaporated to dryness to give 7-(2β-dimethoxymethyl-3α,5α-dihydroxycyclopent-1α-yl)-hept-5-enoic acid 1(5α)-lactone as a gum, $R_F$ = 0.33 (diethyl ether).

The lactone (1.38g.) was dissolved in 0.5N hydrochloric acid (20ml.) and tetrahydrofuran (20ml.), and the solution was left overnight. The solution was cooled in an ice-bath, and neutralised with potassium carbonate (0.7g.). Dimethyl 3-(3-chlorophenoxy)-2-oxopropylphosphonate (2.22g.) was added, then a solution of potassium carbonate (1.05g.) in water (6ml.) was added gradually over 5 minutes. After 30 minutes, further portions of the phosphonate (0.5g.) and potassium carbonate (0.3g.) were added, to complete the reaction. After 2 hours, glyoxylic acid (1.2g.) and potassium carbonate (2.0g.) were added, the mixture was stirred for 30 minutes, then ethyl acetate (25ml.) was added. The ethyl acetate layer was separated and the aqueous layer was washed with ethyl acetate (25ml.). The ethyl acetate solutions were combined, washed with water and dried, and the solvent was evaporated to give a thick gum. The gum was purified by column chromatography on kieselguhr (50g.), eluting with a mixture of 10% by volume of isopropanol in toluene, and collecting 20ml. fractions. Fractions 5, 6 and 7 were combined and evaporated, to give the required lactone starting materials, 16-(3-chlorophenoxy)-9α,11α-dihydroxy-15-oxo-17,18,19,20-tetranor-5-cis,13-trans-prostadienoic acid 1,9α-lactone, $R_F$ = 0.54 (20% by volume of isopropanol in toluene).

EXAMPLE 10

The process described in Example 2 was repeated, using 16-(3-chlorophenoxy)-9α-hydroxy-15-oxo-11α-trimethylsilyloxy-17,18,19,20-tetranor-5cis,13-trans-prostadienoic acid 1,9α-lactone as the starting material, and the reduction was complete after 3 hours. The trimethylsilyl protecting group was removed during the work-up procedure, by stirring the crude product with 2N hydrochloric acid (5ml.) for 30 minutes at room temperature, adding water (10ml.), extracting with ethyl acetate (10ml.), washing the extract with brine and water (1:1 by volume) and evaporating the solvent. The product was hydrolysed with aqueous methanolic potassium hydroxide to give 16-(3-chlorophenoxy)-9α,11α,15-trihydroxy-17,18,19,20-tetranor-5-cis,13-trans-prostadienoic acid which contained 81% of the 15α-hydroxy epimer and 19% of the 15β-hydroxy epimer, by HPLC.

The trimethylsilyl starting material may be prepared from the corresponding 11α-hydroxy starting material described in Example 9, by the silylation process described in the second paragraph of Example 2.

EXAMPLE 11

The reduction process described in Example 2 was repeated, using one equivalent of di-isopropoxy aluminium di-phenylmethoxide as the reducing agent in place of di-isobornyloxyaluminium isopropoxide. After 1½ hours, a further equivalent of the reducing agent was added, and the mixture was stirred for a further 2½ hours. The protecting trimethylsilyl group was removed during the work-up process by stirring the solution of the product with 0.1N hydrochloric acid for 2 hours, and extracting the product as described in Example 10. The product, 4β-[4-(3-chlorophenoxy)-3-hydroxy-1-trans-butenyl]-2,3,3aβ,6aβ-tetrahydro-5α-hydroxy-2-oxocyclopenteno[b]furan was shown by HPLC to contain 95.5% of the α-epimer and 4.5% of the β-epimer.

EXAMPLE 12

4β-[4-(3-Chlorophenoxy)-3-oxo-1-trans-butenyl]-2,3,3aβ,6aβ-tetrahydro-6β-iodo-2-oxo-5α-(trimethylsilyloxy)cyclopenteno[b]furan (134mg.) was stirred in dry toluene (2ml.) under argon at 22° C., and di-isobornyloxy aluminium isopropoxide (1.0ml. of 0.3M solution in toluene) was added over 10 seconds. The mixture was stirred for 2 hours, and water (6 drops) was added, giving a flocculent precipitate which was filtered off through "Hyflo" (kieselguhr filter aid — trade mark) and the filter cake was washed with ethyl acetate (6ml.). The filtrate was washed with a 1:1 by volume mixture of saturated brine and water (2ml.) and dried, and the solvent was evaporated to give a pale orange paste containing the trimethylsilyl enol 4β-[4-(3-chlorophenoxy)-3-hydroxy-1-trans-butenyl]-2,3,3aβ,6aβ-tetrahydro-6β-iodo-2-oxo-5α-(trimethylsilyloxy)cyclopenteno[b]furan, which crystallised on being allowed to stand overnight.

The trimethylsilyl enol was dissolved in ethyl acetate (20ml.), 2N hydrochloric acid (10ml.) was added, and the mixture was stirred for 25 minutes at room temperature to remove the protecting trimethylsilyl group. The ethyl acetate layer was separated, washed with a 1:1 by volume mixture of saturated brine and water (10ml.) and dried, and the solvent was evaporated to give the diol, 4β-[4-(3-chlorophenoxy)-3-hydroxy-1-trans-butenyl]-2,3,3aβ,6aβ-tetrahydro-5α-hydroxy-6β-iodo-2-oxocyclopenteno[b]furan, containing 87% of the α-hydroxy epimer and 13% of the β-hydroxy epimer.

The trimethylsilyl ether used as starting material in the above process may be prepared as follows:

4β-Dimethoxymethyl-2,3,3aβ,6aβ-tetrahydro-5α-hydroxy-6β-iodo-2-oxocyclopenteno[b]furan (1.14g.) was dissolved by stirring under argon at room temperature in a mixture of tetrahydrofuran (8ml.) and water (6.8ml.). 50% v/v Concentrated sulphuric acid (2.4ml.) was added, the mixture was stirred for 2 hours, and cooled at 0° C., and 5N sodium hydroxide (5ml.) was added, followed by potassium carbonate (1.45g.) until the pH was 7–8.

This neutralised solution was added to a solution of dimethyl 3-(3-chlorophenoxy)-2-oxopropylphosphonate (1.35g.) in tetrahydrofuran (6ml.), also cooled to 0° C. The solution was stirred vigorously while a solution of potassium carbonate (1.59g.) in water (5ml.), cooled to 0° C., was added dropwise over 5 minutes, and stirring was continued at 0° C. for 1¼ hours. Glyoxylic acid monohydrate (0.423g.) was added and the solution was stirred for a further 45 minutes at 0° C., adding a further portion of potassium carbonate (276mg.) after the first 15 minutes. The mixture was extracted with ethyl acetate (2 × 10ml.), the extract was washed with a 1:1 by volume mixture of saturated brine and water (3 × 15ml.) and dried, and the solvent was evaporated to give 4β-[4-(3-chlorophenoxy)-3-oxo-1-trans-butenyl-2,3,3aβ,6aβ-tetrahydro-5α-hydroxy-6β-iodo-2-oxocyclopenteno[b]furan, $R_F$ = 0.71 (20% by volume acetone in methylene dichloride).

The product was converted to the required trimethylsilyl ether starting material, $R_F$ = 0.85 (1:1 by volume toluene:ethyl acetate), by the process described in the second part of Example 2.

The enol, 4β-[4-(3-chlorophenoxy)-3-hydroxy-1-trans-butenyl]-2,3,3aβ,6aβ-tetrahydro-6β-iodo-2-oxo-5α-(trimethylsilyloxy)cyclopenteno[b]furan, prepared in the above process, may be converted to the known prostaglandin intermediate 4β-[4-(3-chlorophenoxy)-3-hydroxy-1-trans-butenyl]-2,3,3aβ,6aβ-tetrahydro-2-oxo-5α-(trimethylsilyloxy)cyclopenteno[b]furan as follows:

The enol (107mg.) was stirred in dry toluene (1ml.) under argon at room temperature, tri-n-butyl tin hydride (80μl., 88mg.) was added, and the mixture was stirred at room temperature. After 2½ hours, more tri-n-butyl tin hydride (40μl.) was added, and stirring was continued overnight. Hexane (2ml.) was added, the solution was seeded with 4β-[4-(3-chlorophenoxy)-3α-hydroxy-1-trans-butenyl]-2,3,3aβ,6aβ-tetrahydro-2-oxo-5α-(trimethylsilyloxy)cyclopenteno[b]furan, and left to crystallise. The product, $R_F$ = 0.42 (1:1 by volume toluene:ethyl acetate), was identical with an authentic sample.

EXAMPLE 13

The process described in the first paragraph of Example 12 was repeated at a temperature of −10° C. HPLC assay of the trimethylsilyl enol product indicated 93% of the α-hydroxy epimer and 7% of the β-hydroxy epimer.

EXAMPLE 14

The process described in the first paragraph of Example 12 was repeated at a temperature of −78° C., the reaction was complete in about 5 hours, and the product was deprotected to give the diol, as described in the second paragraph of Example 12, containing 98.5% of the α-hydroxy epimer and 1.5% of the β-hydroxy epimer.

EXAMPLE 15

A solution of 4β-[4-(5-chloropyrid-2-yloxy)-3-oxo-1-trans-butenyl]-2,3,3aβ,6aβ-tetrahydro-5α-hydroxy-2-oxocyclopenteno[b]furan (0.25g.) in dry tetrahydrofuran (3ml.) and dry toluene (2ml.) was stirred and cooled to −78° C., and di-isobornyloxy aluminium isopropoxide (3.8ml. of 0.3M solution in toluene) was added over 10 minutes. After 3 hours, a further portion of the isoproxide (2ml.) was added, and after a further 3 hours, 2N hydrochloric acid was added at −78° C., then the mixture was allowed to warm to room temperature. The organic phase of the reaction mixture was assayed by HPLC directly, and showed 79% of the α-hydroxy epimer and 21% of the β-hydroxy epimer.

The hydroxy-enone starting material used in the above process may be obtained as follows:

Bis(tri-n-butyltin)oxide (27.9g.), polymethylhydrogensiloxane (5.6g.) and toluene (80ml.) were stirred under argon at 60° C. for 30 minutes, 4β- dimethoxymethyl-2,3,3aβ,6aβ-tetrahydro-5α-hydroxy-6β-iodo-2-oxocyclopenteno[b]furan (16.0g.) was added, and the mixture was heated to 80° C. under argon. After 3¾ hours, benzoyl peroxide (750mg.) was added to speed up the reaction, and the reaction was complete 1 hour later. The mixture was cooled to room temperature, and "Filtercell" (trade mark) kieselguhr (1.6g.) and 0.5M aqueous sodium sulphate solution (46ml.) were added. The mixture was stirred for 30 minutes, then filtered through kieselguhr ("Celite"-trade mark). The organic phase was separated, stirred for 10 minutes with a further portion of 0.5M aqueous sodium sulphate solution (46ml.) and filtered through the "Celite" and "Filtercell" from the previous filtration. The aqueous phase was separated, combined with the aqueous phase from the first filtration, stirred for 10 minutes with toluene (5ml.) and filtered through a cotton wool plug, and the aqueous phase, a solution (approximately 90ml.) of the hydroxy-acetal, 4β-dimethoxymethyl-2,3,3aβ,6aβ-tetrahydro-5α-hydroxy-2-oxocyclopenteno[b]furan was separated.

The hydroxy-acetal solution was treated with 1:1 w/w concentrated hydrochloric acid:water to produce an approximately 0.5N hydrochloric acid solution, which was allowed to stand overnight to give a solution of the hydroxyaldehyde, 2,3,3aβ,6aβ-tetrahydro-5α-hydroxy-2-oxocyclopenteno[b]furan-4β-carbaldehyde.

The hydroxy-aldehyde solution was cooled in an ice-bath, and neutralized with potassium carbonate (3.4g.). Dimethyl 3-(5-chloropyrid-2-yloxy)-2-oxo-propylphosphonate (13.7g.) and tetrahydrofuran (80ml.) were added, followed by a solution of potassium carbonate (16.16g.) in water (80ml.) added dropwise over 40 minutes. The mixture was stirred for ½ hour, glyoxylic acid (2.8g.) was added, and the mixture stirred for a further 45 minutes. The reaction mixture was extracted with toluene (120ml.), then a mixture of toluene (25ml.) and ethyl acetate (75ml.). The organic extracts were combined, washed with brine (60ml.) and dried, and the solvent was evaporated. The residue was stirred with toluene for ½ hour, filtered off and dried, to give the required hydroxy-enone starting material, m.p. 130°–133° C.

The dimethyl 3-(5-chloropyrid-2-yloxy)-2-oxopropylphosphonate used in the preparation of the above-mentioned starting material may be obtained as follows:

A mixture of 5-chloropyrid-2-one (18.0g.), ethyl bromoacetate (92.8g.), silver carbonate (20.85g.) and dry toluene (90ml.) was heated at 70° C. for 40 hours, cooled to room temperature and filtered, and the solid product was washed with toluene. The toluene was evaporated under reduced pressure, and the bulk of the excess of ethyl bromoacetate was removed, first by water-pump vacuum and then under high vacuum. The crude product was distilled under high vacuum (0.4 mm.Hg.) yielding ethyl bromoacetate up to 50° C., then three fractions distilling at still-head temperatures of 92°–95°, 95°–97° and 98°–103° C. The second and third fractions consisted of ethyl (5-chloropyrid-2-yloxy)acetate, and were combined.

Dimethyl methylphosphonate (25.0g.) and toluene (150ml.) were stirred under argon and cooled to −73° C., then n-butyl-lithium (80ml. of a 15% w/v solution in hexane) was added over 50 minutes, keeping the temperature below −65° C., followed by a solution of ethyl (5-chloropyrid-2-yloxy)acetate (19.8g.) in toluene (50ml.) added over 15 minutes, also below −65° C. After 1½ hours, the solution was allowed to warm to −10° C., then 2N hydrochloric acid (100ml.) was added gradually, between −10° C. and 10° C. The mixture was stirred for 15 minutes at room temperature and filtered, and the organic phase was separated. The aqueous phase was washed with toluene (50ml.) which was combined with the organic phase. The combined toluene solutions were washed with water (2 × 50ml.) and saturated brine (2 × 50ml.), and were dried. Evaporation of the solvent under reduced pressure, then under high vacuum gave crude phosphonate. The separation aqueous phase was adjusted to pH 6.7 with potassium carbonate and extracted with toluene to yield, after a similar work-up, a further quantity of the phosphonate. Trituration of a sample of the crude product with ether/petrol mixture gave a crystalline product. The remaining crude product was dissolved in diethyl ether (75ml.) with mechanical stirring, the solution was cooled in an ice-bath and seeded, and petroleum ether (b.p. 40°–60° C., 25ml.) was added, followed by a further 25ml., to give dimethyl 3-(5-chloropyrid-2-yloxy)-2-oxopropylphosphonate, m.p. 37°–40° C.

EXAMPLE 16

A solution of the trimethylsilyl enone, 4β-[4-(5-chloropyrid-2-yloxy)-3-oxo-1-trans-butenyl]-2,3,3aβ,-6aβ-tetrahydro-2-oxo-5α-(trimethylsilyloxy)cyclopenteno[b]furan, (9.7g.) in dry toluene (100ml.) was stirred under argon at −78° C. while di-isobornyloxy aluminium isopropoxide (85ml. of a 0.4M solution in toluene) was added over 40 minutes. The mixture was stirred for 6 hours at −78° C., then allowed to warm to room temperature and stirred for 15 minutes. Water (50ml.) was added and the mixture was stirred for 5 minutes, and left to stand overnight. The organic phase was separated, washed with brine (30ml.) and dried, and the solvent was evaporated to give crude 4β-[4-(5-chloropyrid-2-yloxy)-3-hydroxy-1-trans-butenyl]-2,3,3aβ,6aβ-tetrahydro-2-oxo-5α-(trimethylsilyloxy)cyclopenteno[b]furan containing 86% of the α-hydroxy epimer and 14% of the β-hydroxy epimer.

The trimethylsilyl enone used as starting material of the above process may be obtained from the hydroxy enone starting material described in Example 15, by the process described in the second part of Example 2, $R_F = 0.51$ (5% by volume isopropanol in toluene).

What we claim is:

1. A process for the manufacture of a mixture of epimers of the formula:

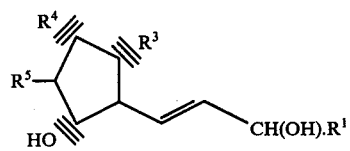

wherein $R^1$ is $C_{4-7}$alkyl, phenoxymethyl optionally substituted in the phenyl ring thereof with halogen or trifluoromethyl, or pyridyloxy methyl optionally substituted by halogen, either $R^3$ is 6-carboxy-2-cis-hexenyl, 6-carboxyhexyl, 6-($C_{1-4}$alkoxycarbonyl)-2-cis-hexenyl, 6-($C_{1-4}$alkoxycarbonyl)hexyl, 6-[tri($C_{1-4}$-alkyl)silyloxycarbonyl]-2-cis-hexenyl or 6-[tri($C_{1-4}$alkyl)silyloxycarbonyl]hexyl and $R^4$ is hydroxy, or $R^3$ and $R^4$ together with the two adjacent ring carbon atoms, form a lactone ring of the formula:

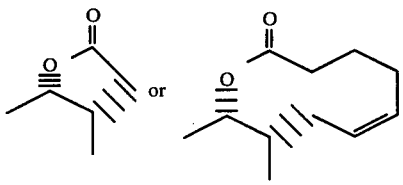

and $R^5$ is hydrogen or iodine, which mixture comprises at least 75% of the side-chain α-hydroxy epimer, characterised in that a ketone of the formula:

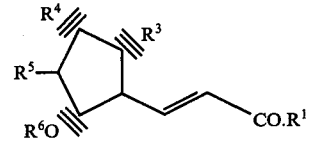

wherein $R^1$, $R^3$ and $R^5$ have the meanings stated above, $R^4$ has the meaning stated above or is tri($C_{1-4}$alkyl)-silyloxy, and $R^6$ is hydrogen, tetrahydropyran-2-yloxy, tri($C_{1-4}$alkyl)silyl, tribenzylsilyl or triphenylsilyl, is reduced with a di-isobornyloxy aluminium $C_{1-4}$ alkoxide or di-isopropoxy aluminium diphenylmethoxide, in an inert solvent at a temperature between +25° C. and −80° C. whereafter, when $R^6$ is other than hydrogen or $R^4$ is tri($C_{1-4}$alkyl)silyloxy, the protecting group is hydrolysed under acidic conditions.

2. The process of claim 1 wherein $R^3$ and $R^4$ together with the two adjacent ring carbon atoms form a lactone ring of the formula:

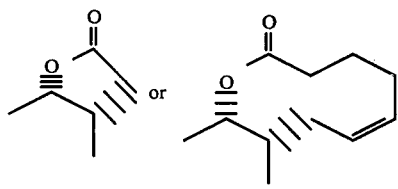

3. The process of claim 1 wherein in the ketone of the formula, V, $R^1$ is 3-chlorophenoxymethyl or 3-trifluoromethylphenoxymethyl.

4. The process of claim 1 wherein, in the ketone of the formula V, $R^1$ is 5-chloropyrid-2-yloxymethyl.

5. The process of claim 1 wherein in the ketone of the formula V, $R^6$ is trimethylsilyl, triethylsilyl, tributylsilyl, triphenylsilyl, tribenzylsilyl or t-butyldimethylsilyl.

6. The process of claim 1 wherein the reducing agent is di-isobornyloxy aluminium isopropoxide.

7. The process of claim 1 wherein the inert solvent is toluene, ethyl acetate or tetrahydrofuran, or a mixture of toluene and ethyl acetate or toluene and tetrahydrofuran.

* * * * *